United States Patent
Tanihara et al.

[11] Patent Number: 5,980,883
[45] Date of Patent: *Nov. 9, 1999

[54] POLYMER GEL FOR MEDICAL USE

[75] Inventors: Masao Tanihara, Ikoma; Yoshimi Kakimaru, Kurashiki, both of Japan

[73] Assignee: Kuraray Co., Ltd., Kurashiki, Japan

[*] Notice: This patent is subject to a terminal disclaimer.

[21] Appl. No.: 08/932,096

[22] Filed: Sep. 17, 1997

[30] Foreign Application Priority Data

Oct. 2, 1996 [JP] Japan ................... 8-281456

[51] Int. Cl.⁶ ............... A61K 31/765; A61K 31/785
[52] U.S. Cl. ................. 424/78.17; 424/78.08
[58] Field of Search ............... 424/78.08, 78.17

[56] References Cited

U.S. PATENT DOCUMENTS 5,599,702  2/1997  Sauber ........................ 435/181
5,658,592  8/1997  Tanihara et al. .
5,679,371  10/1997  Tanihara et al. .
5,770,229  6/1998  Tanihara et al. ............... 424/488

*Primary Examiner*—Peter F. Kulkosky
*Attorney, Agent, or Firm*—Oblon, Spivak, McClelland, Maier & Neustadt, P.C.

[57] ABSTRACT

Provided is a medical material useful for wound dressings or a drug delivery system, which material is safe and has high healing effects, more specifically, which is free from cytotoxicity or other side effects caused by a drug and permits the selective healing of the diseased site in a small dosage without damaging the sites other than the diseased site.

The medical material so provided is a polymer gel having a sequence represented by the formula: A-Sp1-E-Sp2-G wherein A represents a water-swelling polymer gel, Sp1 represents the first spacer, E represents a cleavable group with the main chain to be cleaved via an enzymatic reaction, Sp2 represents the second spacer and G represents a drug. When the polymer gel is used, the cleavable group (E) is cleaved according to an amount of an enzyme existing at the diseased site to release the drug in accordance with the amount of the enzyme.

9 Claims, No Drawings

POLYMER GEL FOR MEDICAL USE

BACKGROUND OF THE INVENTION

1. Field of the Invention

This invention relates to a polymer gel for medical use. More specifically, the present invention relates to a novel polymer gel for medical use having a drug releasing property. The polymer gel of the present invention is useful as the structural component for wound dressings, adhesives for biological tissues, adhesion preventing agents, bone reinforcing materials, and drug releasing base materials.

2. Description of the Related Art

Gauze and/or ointments have been used conventionally for treating wounds such as injury and burn, ulcer, and decubitus. These have effects of absorbing exudate and preventing the penetration of exogenous bacteria and the like. It has been indicated recently that a variety of growth factors (bFGF, TGFβ, etc.) promoting wound healing are present in the exudate from the wounds [see Howell, J. M., Current and Future Trends in Wound Healing, Emerg. Med. Clin. North Amer., 10, 655–663 (1992), etc.] Therefore, attention has been focused on an occlusive dressing having the effect of promoting wound healing while holding the growth factor on the wound [Eaglstein, W. E., Experience with biosynthetic dressings, J. Am. Acad. Dermatol., 12, 434–440 (1985)].

In addition, polymer gels have been used conventionally in various applications in medical fields. It has been proposed recently a drug delivery system (DDS) or wound dressing containing a pharmaceutical agent in a polymer gel.

In recent years, occlusive wound dressings made of polyurethane film, hydrocolloid, alginate gel, polyvinyl alcohol sponge, or polyvinyl alcohol hydrogel have come to be known.

Occlusive wound dressings made of polyurethane film, hydrocolloid, alginate gel or the like are excellent in terms of the effect of facilitating healing. Once the dressings are infected with bacteria, however, the bacteria rapidly proliferate because the wet environment is a suitable medium for the bacteria, with a risk of triggering severe infection. For the prevention or treatment of the infection with bacteria, antibiotics are administered systemically or locally, but blood circulation is so poor at wounds with bacterial infection that an effective dose of antibiotics cannot be delivered to the wounds by the systemic administration, or side effects may occur by local administration due to the cytotoxicity of locally administered antibiotics and healing is prevented.

As wound dressings with pharmaceutical agents contained therein, proposed are a wound contact pad as a part of a wound treating device, comprising a mixture alginate salt of an insoluble alginate salt and a soluble alginate salt, and containing an antibiotics or a local anesthesia [see Japanese Language Laid-Open Publication (PCT) No. 501067/1992]; and a wound dressing containing hydrogel, as the structural component, in which a peptide promoting healing of wounds is covalently bound at least at the surface and/or containing a disinfectant (see Japanese Language Laid-Open Publication (PCT) No. 500028/1994).

In the wound dressings disclosed in the Japanese Language Laid-Open Publication (PCT) No. 501067/1992, drugs such as antibacterial agents and local anesthesia may be contained in a gel pad, but the drugs are consistently released because the drugs are not immobilized onto the gel, thus possibly inducing side effects.

In the wound dressing disclosed in Japanese Language Laid-Open Publication (PCT) No. 500028/1994, the surface thereof is chemically bound with a peptide for promoting wound healing and the bonding cannot be cleaved. Thus, the effect of the peptide can be exerted only at a site in contact to the wound dressing.

Specific examples of the drug delivery system are a crosslinked hyaluronate gel containing lipid microspheres with pharmaceutical agents encapsulated therein and being cleavable with OH radicals [see Yui, et al., Polymer Preprints, Japan, 42(8), 3186–3188 (1993)]; and cellulose powder bound, through an amino acid residue or peptide chain composed of -Phe-, -Tyr-, -Ile-Tyr- or -Gly-Ile-Tyr-, with pholcodine [see F. Lapicque & E. Dellacherie, J. Controlled Release, 4, 39–45 (1986)].

In the former case, the hyaluronate gel is decomposed at a site where OH radicals are generated, whereby a drug encapsulated in lipid microspheres is released. Because the generation of high levels of OH radicals is limited to a certain stage of inflammation or to a very limited area of inflammation, however, the number of diseases to which the system is applicable is relatively limited. Furthermore, the drug encapsulated into lipid microspheres is gradually released from the lipid microspheres into an external aqueous phase so that the drug may be released also at a site besides the diseased site, involving possible side effects.

In the latter case, pholcodine bound through an amino acid residue or peptide chain composed of -Phe-, -Tyr-, -Ile-Tyr- or -Gly-Ile-Tyr- to cellulose powder is tentatively released by the cleaving action of an enzyme, but the release of the drug is as less as 1/1000 to 1/20,000 fold compared with the unimmobilized drug. Thus, such system is not practical.

SUMMARY OF THE INVENTION

Under such situations, there has been a demand for a medical material usable for wound dressings or drug delivery system which material has less cytotoxicity or other side effects caused by a drug and permits selective healing of only the diseased site by a small dosage without damaging the other sites, in short, which material has high safety and has high healing effects.

The present inventors carried out an investigation with a view to developing a medical material being excellent in safety and at the same time having high healing effects compared with the above-described conventional medical materials. Finding that a polymer gel for medical use having a sequence represented by the following formula (II):

$$A\text{-}B\text{-}C\text{-}D \qquad (II)$$

wherein A represents a water-swelling polymer gel, B represents a spacer, C represents a cleavable group with a main chain to be cleaved by an enzymatic reaction and D represents a drug, that is, a polymer gel for medical use produced by immobilizing a drug (D), through a cleavable group (C) with the main chain to be cleaved via an enzymatic reaction and a spacer (B), onto a water-swelling polymer gel (A), exerts a drug releasing property corresponding to the amount of an enzyme, which makes it possible to release a therapeutically effective dose of the drug only at a diseased site generating an enzyme and to treat the diseased site without giving side effects to the other sites, the present inventors already filed a patent application thereon (Japanese Patent Application Laid-Open No. 24325/1996; U.S. Application Ser. No. 08/826,097).

The present inventors have proceeded with an investigation based on the above invention. As a result, it has been found that a polymer gel represented by the formula: A-Sp1-

E-Sp2-G wherein A represents a water-swelling polymer gel, Sp1 represents the first spacer, E represents a cleavable group with the main chain to be cleaved via an enzymatic reaction, Sp2 represents the second spacer and G represents a drug, that is a polymer gel for medical use having spacers between the water-swelling polymer gel and the cleavable group and between the cleavable group and the drug and thus having a novel sequence also exerts a drug releasing property corresponding to the amount of an enzyme so that it can release a therapeutically effective dose of the drug only at the diseased site generating an enzyme and treat the diseased site without giving side effects to the other sites and at the same time has excellent drug release capacity and treatment effects of the diseased site, leading to the completion of the invention.

The present inventors have also found that the above polymer gel for medical use having two spacers can be put on the market even in the form prior to binding with a drug, that is, in the form of a polymer gel represented by the following formula: A-Sp1-E-Sp2' wherein A, Sp1 and E have the same meanings as defined above and Sp2' represents a spacer precursor which can be bound with a drug and a polymer gel for medical use usable effectively for the treatment of a diseased site can be formed by binding a drug with the spacer precursor Sp2' as needed.

In the present invention, there is thus provided a polymer gel for medical use produced by binding a drug with a water-swelling polymer gel in a sequence represented by the following formula (I):

A-Sp1-E-Sp2-G  (I)

wherein A represents a water-swelling polymer gel, Sp1 represents the first spacer, E represents a cleavable group with the main chain to be cleaved via an enzymatic reaction, Sp2 represents the second spacer and G represents a drug.

There is also provided a polymer gel for medical use which has a sequence represented by the following formula (Ia):

A-Sp1-E-Sp2'  (Ia)

wherein A represents a water-swelling polymer gel, Sp1 represents the first spacer, E represents a cleavable group with the main chain to be cleaved via an enzymatic reaction and Sp2 represents the second spacer precursor which can be bound with a drug and which permits the binding of the drug with the water-swelling polymer gel through the first spacer (Sp1), cleavable group (E) and second spacer (Sp2), with the proviso that Sp2 represents the second spacer formed when the second spacer precursor (Sp2') and the drug are bound.

DETAILED DESCRIPTION OF THE PREFERRED EMBODIMENTS

The present invention will hereinafter be described in detail.

In the polymer gel for medical use of the present invention having a sequence represented by the above formula (I) or (Ia), the water-swelling polymer gel (which may hereinafter be called "water-swelling polymer gel (A)") can be used in any form such as form swollen with water, the dry form prior to swelling with water and the form containing a small amount of water but not being swollen completely with water. Accordingly, the polymer gel for medical use according to the present invention embraces any one of the gels in the form swollen with water, the dried form and the form containing a small amount of water.

When a description is made of a polymer gel for medical use in this specification, amino acid residues are sometimes described using abbreviations. The abbreviations of individual amino acid residues used in this specification are shown below in Table 1.

TABLE 1

| Abbreviation | Amino acid residue |
|---|---|
| Ala | L-alanine residue |
| Arg | L-arginine residue |
| Asn | L-asparagine residue |
| Asp | L-aspartic acid residue |
| Cys | L-cysteine residue |
| Gln | L-glutamine residue |
| Glu | L-glutamic acid residue |
| Gly | glycine residue |
| His | L-hystidine residue |
| Ile | L-isoleucine residue |
| Leu | L-leucine residue |
| Lys | L-lysine residue |
| Phe | L-phenylalanine residue |
| Pro | L-proline residue |
| Ser | L-serine residue |
| Thr | L-threonine residue |
| Trp | L-tryptophan residue |
| Tyr | L-tyrosine residue |
| Val | L-valine residue |
| Nle | L-norleucine residue |

In the present specification, the amino acid sequence of a peptide is depicted according to the common method; the amino acid residue at N-terminal is positioned at the left side while the amino acid residue at C-terminal is positioned at the right side. Amino acid residues of D-configuration are shown with its abbreviation followed by the symbol (D) [with (D) at the right side of the abbreviation].

In the polymer gel for medical use of the present invention represented by the above formula (I) or (Ia), the water-swelling polymer gel swells in body fluids such as blood, plasma and extracellular fluid or fluids similar to body fluids such as physiological saline, and also have biocompatibility. In the present invention, no particular limitation is imposed on the polymer material forming the water-swelling polymer gel (A) insofar as it swells in the above body fluid or fluid similar to the body fluid and also has biocompatibility. Examples include polysaccharides such as alginic acid, chitin, chitosan, hyaluronic acid and cellulose and derivatives thereof; proteins such as gelatin, collagen, casein and albumin; polypeptides such as polyaspartic acid, polyglutamic acid and polylysine; and synthetic polymers such as polyvinyl alcohol polymers, ethylene vinyl alcohol copolymers, polyvinylpyrrolidone (PVP) and polyacrylic acid and derivatives thereof. By binding or crosslinking a polymer material or a mixture of two or more of the materials through a covalent bond, hydrophobic bond, hydrogen bond, electrostatic bond or the like, a water-swelling polymer gel can be obtained.

For example, an electrostatically crosslinked gel can be produced by adding a multivalent metal ion such as $Ca^{2+}$ ion to a carboxyl-containing polymer material, such as alginic acid, polyacrylic acid, polyaspartic acid or polyglutamic acid, or a derivative thereof.

Similarly, by mixing such a polymer material containing alginic acid or other carboxyl group with an amino-containing polymer material such as chitosan or polylysine, an electrostatically crosslinked gel can be produced.

By cooling an aqueous solution of gelatin or polyvinyl alcohol, or a derivative thereof, or a solution of gelatin or polyvinyl alcohol, or a derivative thereof in an organic solvent, a gel crosslinked via a hydrogen bond can be produced.

Provided that a polymer material is ethylene vinyl alcohol copolymer or polyacrylic acid, or a derivative thereof, which is dissolved in a water-miscible organic solvent, a solution produced by dissolving the material in a water-miscible organic solvent is immersed in water to generate a gel crosslinked via hydrogen bond and/or hydrophobic bond.

In the case of a polymer material with a reactive group such as alginic acid, polyacrylic acid, chitosan, protein, polylysine, polyaspartic acid, polyglutamic acid or polyvinyl alcohol, or a derivative thereof, a gel crosslinked via a covalent bond can be produced by covalently bonding the polymer material with a multi-functional compound such as lysine oligomer, ethylenediamine, glycerin, succinic acid, oxalic acid or the like. Furthermore, a gel crosslinked via a hydrophobic bond can be produced by bonding the polymer material with a hydrophobic compound such as an alkylated oligopeptide, fatty acid, aliphatic amine or aliphatic alcohol, or a derivative thereof with a hydrophobic compound.

Upon the polymerization of a synthetic polymer material such as polyacrylic acid, polyvinyl alcohol polymers or polyvinylpyrrolidone, or a derivative thereof, a multi-functional monomer such as bisacrylamide or ethylene glycol bismethacrylate may be copolymerized with the synthetic polymer material to generate a covalently crosslinked gel.

As a water-swelling polymer gel (A) for a polymer gel for medical use of the present invention, a gel crosslinked via a hydrogen bond and/or a hydrophobic bond which is obtained by using polyvinyl alcohol as a polymer material is used preferably among the above-exemplified various polymer gels. The polyvinyl alcohol to be used as the polymer material is preferred to have an average polymerization degree of at least 1,500 and a saponification degree of 60 to 100%. From the respect of the strength of the resulting gel, a gel formed of polyvinyl alcohol is preferred to have a syndiotacticity of at least 50% by Dyad convention, with a gel formed of polyvinyl alcohol having a syndiotacticity of at least 53% being more preferred.

The syndiotacticity by dyad convention will be described later more specifically in Examples.

No particular limitation is imposed on the above-described polyvinyl alcohol gel which is preferred in the present invention. Examples include those composed mainly of the polyvinyl alcohol described below in (a) and (b) which pertain to the application of the present applicant. These gels are provided with excellent properties in stability, flexibility, transparency, heat resistance, resistance to moist heat, strength and the like.

(a) Polyvinyl alcohol (Japanese Patent Application Laid-Open No. 206188/1996) having a viscosity-average polymerization degree of at least 300, said polymer having 5 to 50 mole % of a structural unit represented by the following formula (i):

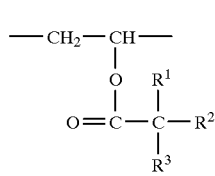

(i)

wherein $R^1$ represents a hydrogen atom or a monovalent hydrocarbon group, $R^2$ and $R^3$ each independently represents a monovalent hydrocarbon group or $R^2$ and $R^3$ are coupled to form a ring together with the adjacent carbon atom, or $R^1$, $R^2$ and $R^3$ are coupled to form a ring together with the adjacent carbon atom; and having a block character (θ) of 0.6 or less, said block character being represented by the following equation (1):

$$\theta = [OH, VES]/2[OH][VES] \quad (1)$$

wherein [OH, VES] represents a molar fraction of methine carbons sandwiched between a hydroxyl-coupled methine carbon and an acyloxy-coupled methine carbon among those of the polyvinyl alcohol, [OH] represents a molar fraction of the vinyl alcohol unit and [VES] represents a molar fraction of the structural unit represented by the above formula (i).

(b) Polyvinyl alcohol (Japanese Patent Application No. 185466/1996) containing the structural unit represented by the above formula (i) in a molar fraction of 0.05 to 0.50; and at the same time, containing at least one structural unit represented by the following formula (ii):

(ii)

wherein X is a group represented by the formula —CO—Y, —Y or —CO—COOH, in which Y represents a hydrocarbon group modified by at least one polar group selected from carboxyl group, sulfonic acid group, amino group and phosphoric acid group, or a hydrocarbon group modified by a group having at least one polar group selected from carboxyl group, sulfonic acid group, amino group and phosphoric acid group, or X forms a phosphoric acid group together with the adjacent oxygen atom, in a molar fraction of 0.0001 to 0.5, preferably in a molar fraction satisfying the following equation (2):

$$[(1-\text{Cest}) \times \text{Cest}] \times 0.01 \leq \text{Cpol} < [(1-\text{Cest}) \times \text{Cest}] \times 2.0 \quad (2)$$

wherein Cpol stands for a molar fraction of the structural unit represented by the formula (2) and Cest stands for a molar fraction of the structural unit represented by the formula (i).

The surface of biological tissues or cells has a hydrogel-like structure containing a large amount of water due to the presence of hydrophilic sugar chains. On the other hand, a hydrogel swollen with water also contains a large amount of water and is therefore in the structure similar to that of biological tissue. Hence, the gel has excellent biocompatibility. However, if the water-swelling degree is too high, the mechanical strength of the gel is lowered. In the case of the water-swelling polymer gel (A) in the polymer gel for medical use according to the present invention, the weight of the hydrogel which has been swollen with water to equilibrium is preferably in a range of 1 to 1,000, more preferably in a range of 10 to 200, provided that the dry weight of the polymer material prior to swelling with water is defined as 1.

In the polymer gel for medical use of the present invention represented by the above formula (I) [which may hereinafter be called "polymer gel (I)"], a cleavable group (E) with the main chain to be cleaved via an enzymatic reaction [which may hereinafter be called "cleavable group (E)" simply] is coupled with a water-swelling polymer gel (A) through the first spacer (Sp1) [which will hereinafter be called "first spacer (Sp1)] and a drug is coupled with the cleavable group (E) through the second spacer (Sp2) [which will hereinafter be called "second spacer (Sp2)].

In the polymer gel for medical use of the present invention represented by the above formula (Ia) [which may hereinafter be called "polymer gel (Ia)"], a cleavable group (E) is coupled with a water-swelling polymer gel (A) through the first spacer (Sp1) and the second spacer precursor (Sp2') [which will hereinafter be called "second spacer precursor (Sp2')] is coupled with the cleavable group (E). By coupling the second spacer precursor (Sp2') with a drug, in this polymer gel (Ia), the above-described polymer gel (I) is formed.

Incidentally, the polymer gel (I) and polymer gel (Ia) may be called "polymer gel" collectively.

The term "main chain" as used herein means a bonding chain composed of atoms which directly take part in the bonding of a drug to a water-swelling polymer gel (A). When a cleavage occurs at any position of the main chain, the drug is released from the polymer gel.

In the polymer gel according to the present invention, no particular limitation is imposed on the cleavable group (E) with the main chain to be cleaved by an enzymatic reaction, it is a group whose main chain is specifically cleaved with an enzyme present at a diseased site. The kind of the cleavable group (E) differs, depending on the diseased site to which the polymer gel is applied. Examples of the enzyme present in the diseased site include peptide hydrolase such as elastase, cathepsin G, cathepsin E, cathepsin B, cathepsin H, cathepsin L, trypsin, pepsin, chymotrypsin and γ-glutamyltransferase (γ-GTP); sugar chain hydrolase such as phosphorylase, neuraminidase, dextranase, amylase, lysozyme and oligosaccharidase; and oligonucleotide hydrolases such as alkaline phosphatase, endoribonuclease and endodeoxyribonuclease. In addition, other enzymes which are present at a diseased site and specifically cleave the main chain can also be adopted.

Examples of the cleavable group (E) in the polymer gel include, but not limited to, amino acid residues such as -Arg-, -Ala-, -Ala(D)-, -Val-, -Leu-, -Lys-, -Pro-, -Phe-, -Tyr- and -Glu-; 2-mer to 6-mer oligopeptides such as -Ile-Glu-Gly-Arg-, -Ala-Gly-Pro-Arg-, -Arg-Val-(Arg)$_2$-, -Val-Pro-Arg-, -Val(D)-Pro-Arg-, -Gln-Ala-Arg-, -Gln-Gly-Arg-, -Asp-Pro-Arg-, -Gln-(Arg)$_2$-, -Phe-Arg-, -(Ala)$_2$-, -Ala-Ala(D)-, -(Ala)$_2$-Pro-Val-, -(Val)$_2$-, -(Ala)$_2$-Leu-, -Gly-Leu-, -Phe-Leu-, -Val-Leu-Lys-, -Gly-Pro-Leu-Gly-Pro-, -(Ala)$_2$-Phe-, -(Ala)$_2$-Tyr-, -(Ala)$_2$-His-, -(Ala)$_2$-Pro-Phe-, -Ala-Gly-Phe-, -Asp-Glu-, -(Glu)$_2$-, -Ala-Glu-, -Ile-Glu-, -Gly-Phe-Leu-Gly-, -(Arg)$_2$-, -Phe-Pro-Arg-, -Phe(D)-Pro-Arg-, -Tyr-Pro-Arg- and -Tyr(D)-Pro-Arg-; D-glucose, N-acetylgalactosamine, N-acetylneuraminic acid, N-acetylglucosamine and N-acetylmannosamine, and oligosaccharides thereof; and oligoribonucleic acids such as oligodeoxyadenine, oligodeoxyguanine, oligoguanine, oligocytosine and oligouridine.

Among them, amino acid residues or 2-mer or 6-mer oligopeptide residues are preferably used as the cleavage group (E) from the respect of the readiness of enzyme cleavage and the safety for living bodies. In addition, it is preferred that the cleavage site by an enzyme (a carboxyl terminal of the oligopeptide residue) is preferably Arg. More preferably, an oligopeptide residue selected from -Val-Pro-Arg-, -Val(D)-Pro-Arg-, -Phe-Pro-Arg-, -Phe(D)-Pro-Arg-, -Tyr-Pro-Arg- and -Tyr(D)-Pro-Arg- can be used. It is particularly preferred that the third amino acid (p3) from the cleavage site in the direction of an N-terminal is an aromatic amino acid residue such as Phe or Tyr, with D aromatic amino acid such as Phe(D) and Tyr(D) being more preferred. More specifically, -Phe-Pro-Arg- and -Tyr-Pro-Arg- are preferred, with -Phe(D)-Pro-Arg- and -Tyr(D)-Pro-Arg- being particularly preferred.

For increasing the cleavage property of the cleavage group (E) by an enzyme, it may be a group composed of at least two sequences, each having at least one group with the main chain to be cleaved by an enzymatic reaction, coupled in series. Examples of such cleavage group (E) include -Val-Pro-Arg-Gly-Val-Pro-Arg-Gly-Val-Pro-Arg-, -Phe-Pro-Arg-Gly-Phe-Pro-Arg- and -Phe(D)-Pro-Arg-Gly-Phe(D)-Pro-Arg-.

The first spacer (Sp1), second spacer (Sp2) and second spacer precursor (Sp2') in the polymer gels (I) and (Ia) of the present invention control the reactivity between the enzyme and cleavage group (E). These spacers and spacer precursor themselves are not cleaved by the enzyme. No particular limitation is imposed on the kind or structure of the first spacer (Sp1) and the second spacer (Sp2) insofar as they serve for an enzyme present at a diseased site to react with the cleavage group (E) in an appropriate manner. On the second spacer precursor (Sp2') in the polymer gel (Ia), on the other hand, no particular limitation is imposed insofar as it can form the second spacer (Sp2) coupled with a drug.

It has been confirmed by the present inventors that if no spacer is used, cleavage reaction of the cleavage group (E) by an enzyme shows a marked deterioration.

In general, if the number of the atoms, such as carbon, nitrogen and oxygen, in the main chain of the spacer is small, the reactivity of the enzyme with the cleavable group (E) is lowered due to the steric hindrance of the water-swelling polymer gel (A), causing the decrease in the release of the drug. If the total number of the atoms constituting the main chain of the spacer is below 3, the release of a therapeutically effective amount of the drug may not be expected. If the total number of the atoms constituting the main chain of the spacer is increased, on the other hand, the reactivity of the enzyme with the cleavable group (E) is increased, which makes it possible to increase the release of a therapeutically effective amount of the drug. If the total number of the atoms constituting the main chain of the spacer is above 20, the spacer may eventually take a conformation such as a turn structure and α-helix; and the spacer takes such form, the cleaving action of the enzyme on the cleavable group (E) may be lowered. Furthermore, the spacer may aggregate due to inter-spacer and/or intra-spacer hydrophobic interaction, causing a decrease in the cleaving action of the enzyme on the cleavable group (E).

Therefore, in order to properly control the cleaving action of the enzyme on the cleavable group (E), thereby permitting the release of the drug in a suitable amount, it is preferred that any one of the first spacer (Sp1), the second spacer (Sp2) and the second spacer precursor (Sp2') is a molecular chain with the total number of carbon atoms, nitrogen atoms and oxygen atoms contained in the main chain being at least 4; more preferably, the spacer is a molecular chain with the total being 4 to 20; and most preferably, the spacer is a molecular chain with the total being 6 to 18.

In any one of the first spacer (Sp1), the second spacer (Sp2) and the second spacer precursor (Sp2'), a spacer with a polar group such as a hydroxy group tends to elevate the cleaving action of the enzyme on the cleavable group (E), thereby increasing the release of the drug.

Since some spacers different in kind or structure excessively increase the reactivity of the enzyme with the cleavable group (E) and cause the release of the drug at an unnecessary level, it is desirable to select a spacer suitable for the diseased site.

In the polymer gel of the present invention, the first spacer (Sp1) is interposed between the water-swelling polymer gel (A) and the cleavable group (E) and the second spacer (Sp2)

is interposed between the cleavable group (E) and a drug. Compared with the polymer gel having only the first spacer, it is therefore possible to improve the selectivity of the cleaving action of the enzyme on the cleavable group (E) by selecting two spacers (Sp1) and (Sp2) from the viewpoint of the kind, structure, the length of the main chain or the like and then using them in combination, thereby obtaining a polymer gel more suited to the kind or the condition of the diseased site.

Moreover, since the polymer gel of the present invention has the first spacer (Sp1) and second spacer (Sp2), even in the case where the drug is not easily bound directly with the cleavable group (E), the drug can be bound easily by selecting as the second spacer (Sp2) a proper one. In this point, compared with the polymer gel containing only the first spacer (Sp1), the use of two spacers in combination makes it possible to widen the range of a drug to be bound, thereby widening the application range and heightening usefulness of the resulting polymer gel.

Examples of the first spacer (Sp1) and the second spacer (Sp2) include linear molecular chains such as a methylene group which may or may not have a substituent, an ether bond, a peptide bond, an imino bond and a C=C double bond. Specific examples include:

—CO—(CH$_2$)$_2$—CO—,
—CO—(CH$_2$)$_2$—CO—NH—CH$_2$—CO—,
—CH$_2$—CO—NH—(CH$_2$)$_2$—NH—CO—(CH$_2$)$_2$—CO—,
—CH$_2$—CH(OH)—CH$_2$—NH—CO—(CH$_2$)$_2$—CO—,
—CH$_2$—CH(OH)—CH$_2$—NH—(CH$_2$)$_2$—NH—CO—(CH$_2$)$_2$—CO—,
—NH—(CH$_2$)$_2$—NH—CO—CH$_2$—NH—CO—(CH$_2$)$_2$—CO—,
—NH—(CH$_2$)$_2$—NH—CO—CH$_2$—NH—CO—(CH$_2$)$_3$—CO—,
—CO—(CH$_2$)$_2$—NH—CO—CH$_2$—NH—CO—(CH$_2$)$_2$—CO—,
—NH—(CH$_2$)$_2$—NH—CO—CH$_2$—NH—CO—(CH$_2$)$_2$—CO—,
—NH—(CH$_2$)$_2$—NH—CO—CH$_2$—NH—CO—(CH$_2$)$_3$—CO—,
—NH—(CH$_2$)$_2$—NH—CO—CH(CH$_3$)—NH—CO—(CH$_2$)$_2$—CO—,
—NH—(CH$_2$)$_2$—NH—CO—CH(CH$_2$OH)—NH—CO—(CH$_2$)$_2$—CO—,
-Gly-Phe-Pro-Ala-Gly-Gly-,
-Gly-Tyr-Pro-Ala-Gly-Gly-,
-Gly-Phe-Pro-Ala-,
-Gly-Phe-, and
-Gly-Gly-.

It is preferred that each of the first spacer (Sp1) and the second spacer (Sp2) is any one of —CO—(CH$_2$)$_2$—CO—, —CO—(CH$_2$)$_2$—CO—NH—CH$_2$—CO—, —NH—(CH$_2$)$_2$—NH—CO—CH$_2$—NH—CO—(CH$_2$)$_2$—CO—, -Gly-Phe-Pro-Ala-Gly-Gly-, -Gly-Tyr-Pro-Ala-Gly-Gly-, -Gly-Phe-Pro-Ala-, -Gly-Phe- and -Gly-Gly- among the above-exemplified ones.

The first spacer (Sp1) and the second spacer (Sp2) may be the same or different but it is more preferred that the first spacer (Sp1) is —CO—(CH$_2$)$_2$—CO— or —CO—(CH$_2$)$_2$—CO—NH—CH$_2$—CO— and the second spacer is any one of -Gly-Phe-Pro-Ala-Gly-Gly-, -Gly-Tyr-Pro-Ala-Gly-Gly-, -Gly-Phe-Pro-Ala-, -Gly-Phe- and -Gly-Gly-.

As the second spacer precursor (Sp2') in the polymer gel (Ia), preferred are, among the above-exemplified spacers, those having at their terminal (right terminal) a residue reactive to a drug.

Each of the first spacer (Sp1), the second spacer (Sp2), the second spacer precursor (Sp2') and cleavable group (E) can be prepared, in accordance with the kind of the group, by the ordinary organic synthesis.

When it is an oligopeptide residue, it is prepared by a method generally employed for peptide synthesis, such as solid phase synthesis and liquid phase synthesis (see for example, "Biochemistry Experimental Course, second series, No. 2, Protein Chemistry (2)", pp. 641–694, Nippon Biochemistry Association eds., issued by Tokyo Kagaku Dojin Kabushiki Kaisha, On May 20, 1987.). When it is an oligosaccharide residue, it is prepared by usual methods employed for the synthesis or extraction of sugar chain (see for example, "New Biochemistry Experimental Course, No. 3, Sugar (I)," pp. 95–140 and pp. 421–438(1990), Nippon Biochemistry Association eds., issued by Tokyo Kagaku Dojin Kabushiki Kaisha). When it is an oligonucleic acid residue, it is prepared by a method generally employed for the synthesis or extraction of a nucleic acid, (see for example, "New Biochemistry Experimental Course, No. 2, Nucleic Acids (III)," pp. 254–269(1992), Nippon Biochemistry Association eds., issued by Tokyo Kagaku Dojin Kabushiki Kaisha; and "New Biochemistry Experimental Course, No. 2, Nucleic Acids (I), "pp. 147–168(1991), Nippon Biochemistry Association eds., issued by Tokyo Kagaku Dojin Kabushiki Kaisha.

In the polymer gel of the present invention, a drug [which may hereinafter be called "drug (G)"] bound through the second spacer (Sp2) can be selected as needed depending on the purpose of the polymer gel and no particular limitation is imposed on it.

For example, if the polymer gel of the present invention is used as a wound dressing, adhesive for biological tissues, and an adhesion preventing agent, the drug used may be an antibacterial agent such as disinfectant or antibiotic; a blood flow modifying agent such as actosin or prostaglandin E1 (PGE1); an anti-inflammatory and analgesic agent such as steroid or indomethacin; a growth factor such as transforming growth factor β(TGFβ), platelet-derived growth factor (PDGF) or fibroblast growth factor (FGF); or an enzyme inhibitor such as urinastatin or tissue inhibitor of metalloproteinase (TIMP). When the polymer gel of the present invention is used as a bone reinforcing material, the drug used may be, for example, a bone cell growth factor such as bone morphogenetic protein (BMP), TGFβ or parathyroid hormone (PTH); Interleukin -1 (IL-1) inhibitor; or a bone resorption suppressing factor such as bisphosphonate or calcitonin. When the polymer gel of the present invention is used as a drug releasing material, the drug used may be an anticancer agent such as neocarzinostatin or adriamycin; or an anti-inflammatory agent such as steroid or non-steroidal inflammatory agent.

Since in the polymer gel of the present invention, the cleavable group (E) is cleaved depending on an enzyme level generated at a diseased site and the drug is released in accordance with the enzyme level, the amount of the drug to be immobilized is not strictly limited. However, it is required to immobilize a minimum amount of the drug capable of exerting the therapeutic effect at a diseased region. The amount of the drug to be immobilized can be controlled by the introduction ratio of the first spacer (Sp1) into a water-swelling polymer gel (A).

When the introduction amount of the first spacer (Sp1) is too small, an effective amount of the drug cannot be immobilized. Alternatively, when the introduction amount of the first spacer (Sp1) is too great, the properties of the water-swelling polymer gel may be altered. Therefore, too small or large amount is not preferred. Thus, the introduction ratio of the first spacer (Sp1) into a water-swelling polymer gel is, in general, preferred to be at least 0.05 μmol, more preferably 0.2 to 50 μmol, per ml. water-swelling polymer gel (polymer gel swollen with water to equilibrium), though depending on the kind of the drug or cleavage readiness of the cleavable group (E) by an enzyme. The introduction ratio of the first spacer (Sp1) should be determined, for example, by measuring the amount of the amino group in an intermediate product by the ninhydrin method [see Sarin, V. K. et al., Anal. Biochem., 117, 147–157(1981)].

In the polymer gel of the present invention, the cleavable group (E), the second spacer (Sp2) or the second spacer precursor (Sp2'), and the drug are bound to the water-swelling polymer gel (A) through the first spacer (Sp1) so that each of the introduction ratios of the cleavable group (E), the second spacer (Sp2) or the second spacer precursor (Sp2') and the drug is determined by the introduction ratio of the first spacer (Sp1) and generally is the same or less than that of the first spacer (Sp1).

In the polymer gel of the present invention, a method for immobilizing a drug, through the first spacer (Sp1), the cleavable group (E) and the second spacer (Sp2), onto a water-swelling polymer gel (A), preferably comprises a covalent process. As the immobilization method, known activation methods or reaction methods, generally employed for immobilized enzymes and affinity chromatography can be used. Examples of the reaction for immobilization (bonding) include, but not limited to, a dehydration condensation reaction using a condensing agent such as 1-ethyl-3-(3-dimethylaminopropyl)-carbodiimide hydrochloride salt or -dicyclohexylcarbodiimide; a decarbonate reaction using an alkali catalyst; an ammonolysis reaction of epoxy groups; an ester exchange reaction; and an urethane bond forming reaction. In general, it is preferred that the second spacer (Sp2) and the drug are bound together via an ester bond, an ether bond or a peptide bond, because in this case, the cleavable group (E) is cleaved by the enzymatic action so that the drug efficacy is exhibited effectively without a serious influence on the chemical structure of the drug at the time when the drug is released.

No particular limitation is imposed on the order of the reaction insofar as the polymer gel having the sequence represented by (I) or (Ia) is formed. For example, the polymer gel (I) can be obtained by any one of the methods exemplified below:

(1) a method in which the first spacer (Sp1), a cleavable group (E), the second spacer (Sp2) and a drug (G) are reacted in order of mention with the water-swelling polymer gel (A);

(2) a method in which the water-swelling polymer gel (A) is bound with a sequence of the first spacer (Sp1), a cleavable group (E), the second spacer (Sp2) and a drug (G) bound in advance in order of mention;

(3) a method in which a sequence of a cleavable group (E), the second spacer (Sp2) and a drug (G) bound in advance in order of mention is bound with another preliminarily-bound sequence of the water-swelling polymer gel (A) and the first spacer (Sp1);

(4) a method in which a preliminarily-bound sequence of the second spacer (Sp2) and a drug (G) is bound with another sequence of the water-swelling polymer gel (A), the first spacer (Sp1) and a cleavable group (E) preliminarily bound in order of mention; and (5) a method in which with the water-swelling polymer gel (A) bound with one portion of the first spacer (Sp1) (which has not yet finished the binding), a preliminarily bound sequence of the remaining portion of the first spacer (Sp1), a cleavable group (E) and the second spacer (Sp2) are bound, and then a drug (G) is bound with the second spacer (Sp2).

Among the above-exemplified methods, the methods of (3) and (5) are preferred owing to a good binding efficiency.

The polymer gel of the present invention may contain, as needed, a metal ion such as $Ca^{2+}$ ion, having a pharmaceutical action and a pharmaceutically acceptable additive such as gel softening agent and stabilizing agent, for example, glycerin or polyethylene glycol, depending on the objective. The polymer gel of the present invention may be used after swollen with a physiologically acceptable solution such as glucose solution or physiological saline as needed. At this time, the solution may contain various pharmaceutically acceptable additives. Furthermore, if the exudate such as body fluid is at a higher level, the polymer gel of the present invention may be applied in the dry state.

When the drug to be immobilized on to the polymer gel has not so high stability under wet conditions, the polymer gel onto which the drug has been immobilized may be stored or distributed under dry conditions.

No particular limitation is imposed on the using form or administration form of the polymer gel of the present invention. It can be used, for example, as an external preparation such as dressing, adhesive or adhesion preventing agent, a bone reinforcing agent or a base material for sustained release of a drug. If the gel is administered as a bone reinforcing agent, the gel can be administered into bone cavity, or into the cross section of a bone fracture site. If the gel is administered as a base material for sustained release of a drug, the gel can be administered via subcutaneous administration, intraperitoneal administration, intravascular administration, percutaneous administration, oral administration or intravascular administration.

The polymer gel in accordance with the present invention may take an application form suitable for the objective of gel application or administration form, such as sheet, film, fiber, woven fabric, non-woven fabric, knitted cloth, net, liquid, powder or sponge. By molding the polymer gel of the present invention into a plate form or a particle form, wound dressings may be obtained. Alternatively, by molding the gel as described above and then attaching the molded gel with a film made of a polyurethane resin or a silicone resin followed by addition or coating of an adhesive, wound dressings may also be produced. Because the would dressings from the polymer gel of the present invention are flexible due to the higher water content, less physical irritation may be induced on wounds with less pain to the patient. Furthermore, because the wound dressings have excellent water retentivity, the dressings may be exchanged less frequently, with the decrease in patient pain, care, and wound damage, while greatly retaining the healing promoting factor in the exudate with no inhibition of the function of the factor, thereby promoting the healing of the wound.

In the polymer gel of the present invention, as is represented by the above formula (I), a drug is immobilized onto a water-swelling polymer gel (A) through a spacer and a cleavable group (E) so that the main chain of the cleavable group (E) can be cleaved by the action of an enzyme existing at a diseased site and the drug is released smoothly.

In the polymer gel of the present invention, as described above, the first spacer (Sp1) and the second spacer (Sp2) are interposed between a water-swelling polymer gel (A) and a cleavable group (E) and between the cleavable group (E) and a drug, respectively, as can be understood from the formula (I), which makes it possible to improve the selectivity of the cleaving action of an enzyme on the cleavable group (E), to obtain a polymer gel more suited to the kind or the condition of the diseased site. Even if the drug is not easily bound with the cleavable group (E) directly, the drug can be bound more easily by selecting a suitable one as the second spacer (Sp2).

If a drug is immobilized directly onto a water-swelling polymer gel (A) through a cleavable group (E), on the other hand, the cleaving reaction of the main chain of the cleavable group (E) by an enzyme is very slow, so that a therapeutically effective amount of the drug cannot be released. If the drug is bound with a water swelling-polymer gel (A) only through a spacer without a cleavable group (E), the enzyme does not act for cleavage and the drug is not successfully released at a diseased site.

For example, if use is made of the polymer gel of the present invention obtained by immobilizing a drug (such as an anti-inflammatory agent or antibiotic) through a cleavable group (E) [for example, an oligopeptide such as -(Ala)$_3$-, -(Ala)$_2$-Pro-Val- or -(Ala)$_2$-Phe-] to be cleaved with an enzyme (elastase, cathepsin G or the like) generated by neutrophils, the cleavage group is cleaved and the drug is released, only at an inflammatory site infiltrated and activated with the neutrophils, at an amount corresponding to the level of the enzyme present at the site, triggering the anti-inflammatory action and the antibacterial action of the drug.

If use is made of the polymer gel of the present invention obtained by immobilizing an antibiotic such as gentamycin or norfloxacin through a cleavable group (E) [for example, -Asp-Glu- or -Ala-Gly-Phe-) to be cleaved with an enzyme (Staphylococcal serin proteinase, Staphylococcal cysteine proteinase, or the like) generated by bacteria or an enzyme (Thrombin or the like) activated by a substance (Staphylocoagulase or the like) having an enzyme activating action, the antibiotic may be released only at an infected site during the development of such infection, whereby the antibacterial action is triggered.

If use is made of the polymer gel of the present invention obtained by immobilizing a blood flow modifying agent such as actosin or PGE1 through a cleavable group (E) [for example, -(Ala)$_2$-Phe-, -(Ala)$_2$-Pro-Phe-, -Ala-Gly-Phe-, -Phe- or -Tyr-) to be cleaved with an enzyme (cathepsin E, pepsin or the like) which is activated under acidic conditions, the drug is released at a site with poor blood flow so as to improve the blood flow.

If use is made of the polymer gel of the present invention obtained by immobilizing an anticancer agent through a cleavable group (E) (for example, -Gly-Phe-Leu-Gly-, -(Arg)$_2$-, -Phe-Arg-, phosphate diester bond or the like) to be cleaved with an enzyme (alkaline phosphatase, γ-glutamyltransferase (γ-GTP), cathepsin B, cathepsin H, cathepsin L) generated by cancer cells, the drug is released only around the cancer cells, triggering the anti-cancer action.

In any of the above-described cases, the cleavable group (E) is not cleaved and the drug is not released or is released in a trace amount at a normal site where no enzyme for cleaving the cleavage group (E) is generated or during the period without such generation. Therefore, side effects due to the toxicity of the drug can be suppressed at minimum.

It has been confirmed by toxicity tests that the polymer gel of the present invention has little toxicity. It has also been confirmed that the polymer gel of the present invention is stable under storage.

As described above, in the polymer gel of the present invention, a drug is immobilized onto a water-swelling polymer gel (A) through a spacer and a cleavable group (E) so that the main chain of the cleavable group (E) is cleaved in accordance with the amount of the enzyme existing in the diseased site and drug release properties are exhibited in accordance with the amount of the enzyme. It is therefore possible to release an amount of the drug effective for the treatment at only the diseased site generating an enzyme, thereby carrying out the healing of the diseased site smoothly while controlling the side effects of the drug at the minimum level.

The polymer gel of the present invention is characterized in that the first spacer (Sp1) and the second spacer (Sp2) are interposed between a water-swelling polymer gel (A) and a cleavable group (E) and the cleavable group (E) and a drug (G), respectively, which makes it possible to improve further the selectivity of the cleaving action of an enzyme on the cleavable group (E), to obtain a polymer gel more suited to the kind or condition of the diseased site, and to immobilize the drug on the water-swelling polymer gel (A) more smoothly by selecting a proper one as the second spacer (Sp2) even if the drug is not easily bound with the cleavable group (E) directly.

The polymer gel of the present invention is useful as the structural component for wound dressings, adhesives for biological tissues, adhesion preventing agents, bone reinforcing agents, and drug releasing base materials. For treatment of inflammation and healing promotion thereof, the gel can be applied to sites of wounds including general wounds such as scar, cut and acne; artificial dermal defects such as dermatome wounds and dermabrasion wounds, surgery wounds such as cut wounds; burn; ulcer; and decubitus. Furthermore, the gel can be applied also to adhesion of wounds or organs after surgery, prevention of adhesion of wounds to other tissues after surgery, bone reinforcement for osteoporosis and bone fracture, and treatment of malignant neoplasm.

EXAMPLES

The present invention will hereinafter be described more specifically by examples. It should however be borne in mind that the present invention is not limited to or by the following examples.

Referential Example 1

Preparation of a water-swelling polymer gel (polyvinyl alcohol gel)

(1) In a reaction vessel equipped with an agitator, 200 g of vinyl pivalate and 70 g of methanol were charged, followed by purging with a nitrogen gas. Separately, 0.04 g of 2,2'-azobisisobutylonitrile was dissolved as a polymerization initiator in 5 g of methanol, followed by purging with a nitrogen gas. When the internal temperature of the reaction vessel was increased to 60° C. by heating, the solution of the polymerization initiator prepared above was added to start the polymerization. Polymerization was carried out for 5 hours at the same temperature. When the polymerization ratio reached 40%, the reaction mixture was cooled to 20° C. to terminate the polymerization. While t-butanol was added to the reaction mixture in portions, the unreacted portion of vinyl pivalate was distilled off under reduced pressure, whereby a solution of polyvinyl pivalate in t-butanol was collected. To the resulting solution, an adequate amount of tetrahydrofuran was added. From the resulting mixture, t-butanol was distilled off under reduced pressure, whereby a solution of polyvinyl pivalate in tetrahydrofuran (concentration: 45.7 wt. %) was obtained.

(2) In a reactor equipped with an agitator and a reflux condenser, 50 g of the solution of polyvinyl pivalate in tetrahydrofuran, which had been obtained above, were charged and heated to 60° C., followed by purging with a nitrogen gas. At the temperature kept at 60° C., 20 g of a 25% solution of potassium hydroxide, which had been prepared separately and purged with nitrogen, were added, followed by thorough stirring. The reaction mixture became a gel after about 30 minutes. After the reaction mixture was kept at 60° C. for further 6 hours, 5.5 g of acetic acid and 5.5 g of methanol were added to neutralize the potassium hydroxide. The resulting gel was then pulverized, followed by Soxhlet washing with methanol, whereby a partially-saponified polyvinyl alcohol containing a structural unit (i) (vinyl ester unit) was prepared.

(3) Concerning the partially saponified polyvinyl alcohol obtained above in (2), the molar fractions of the structural unit (i) and the vinyl alcohol unit were measured in accordance with the method which will be described later. As a result, the molar fraction of the structural unit (i) was 0.19, while that of the vinyl alcohol unit was 0.81.

Measurement of the Molar Fractions of the Structural Unit (i) and Vinyl Alcohol Unit In a mixed solvent of 1.0 g of deuterated dimethyl sulfoxide and 0.2 g of deuterated chloroform, 0.01 g of the partially saponified polyvinyl alcohol obtained above in (2) and having the structural unit (i) was dissolved. By proton NMR measurement of the resulting solution by an NMR spectrometer ["JNM-GSX270", trade name; product of JEOL Ltd.], the molar fractions of the structural unit (i) and vinyl alcohol unit in the polyvinyl alcohol were measured.

(4) The viscosity average polymerization degree of the partially saponified polyvinyl alcohol obtained above in (2) was 1650 as measured by the following method:

Measurement of the Viscosity Average Polymerization Degree of a Partially Saponified Polyvinyl Alcohol In 10 g of methanol, 2 g of the partially saponified polyvinyl alcohol obtained above in (2) were dissolved, followed by the addition of 1.6 g of potassium hydroxide. The resulting solution was heated at 60° C. for 120 minutes to completely saponify the ester bond including the structural unit (i) of the polyvinyl alcohol. To 1 g of the resulting completely saponified polyvinyl alcohol, 30 g of acetic anhydride and 6 g of pyridine were added, followed by hermetical sealing. By heating at 110° C. for 5 hours, the hydroxyl group in the polyvinyl alcohol was completely made into acetate ester, followed by the addition of n-hexane to precipitate the resulting polyvinyl acetate. The precipitate was then dissolved in acetone, followed by the addition of n-hexane to cause precipitation, which procedure was repeated twice for the purification. In 80 g of acetone, 0.4 g of the resulting purified polyvinyl acetate was dissolved and the intrinsic viscosity [η] at 30° C. of the resulting solution was measured. In accordance with the following equation (3), the viscosity average polymerization degree was determined.

$$P = \{[\eta] \times (1000/7.94)\}^{(1/0.62)} \quad (3)$$

wherein P represents a viscosity average polymerization degree of a partially saponified polyvinyl alcohol.

(5) The syndiotacticity of the partially saponified polyvinyl alcohol which had been obtained above in (2) and had the structural unit (i) was measured by the method which will be described below. As a result, the syndiotacticity by dyad tactility convention determined in accordance with the following equation (4) was 61%.

$$\text{Dyad tacticity} = S + (H/2) \quad (4)$$

wherein S and H represent syndiotacticity and heterotacticity in a triad tacticity determined from proton NMR, respectively.

Measurement of Syndiotacticity

In 1 g of deuterated dimethyl sulfoxide, 0.01 g of purified polyvinyl alcohol similar to that used for the measurement of the viscosity average polymerization degree was dissolved. The syndiotacticity and heterotacticity in a triad tacticity which have been determined from a signal of a hydroxyl group proton in proton NMR spectrum of the resulting solution were measured by an NMR spectrometer ("JNM-GSX270", trade name; product of JEOL Ltd.). Based on the above equation (4), the syndiotacticity by dyad tacticity convention was determined, which was designated as a syndiotacticity of the partially saponified polyvinyl alcohol having the structural unit (i).

EXAMPLE 1

Preparation of a Polymer Gel

In Example 1, prepared was a polymer gel comprising a gel, which was composed of the polyvinyl alcohol obtained in (2) of Referential Example 1, as a water-swelling polymer gel (A), —CO—(CH$_2$)$_2$—CO—NH—CH$_2$—CO— as the first spacer (Sp1), -Phe(D)-Pro-Arg- as a cleavable group (E), -Gly-Phe-Pro-Ala-Gly-Gly- as the second spacer (Sp2) and gentamycin as a drug; and being represented by the following formula (III):

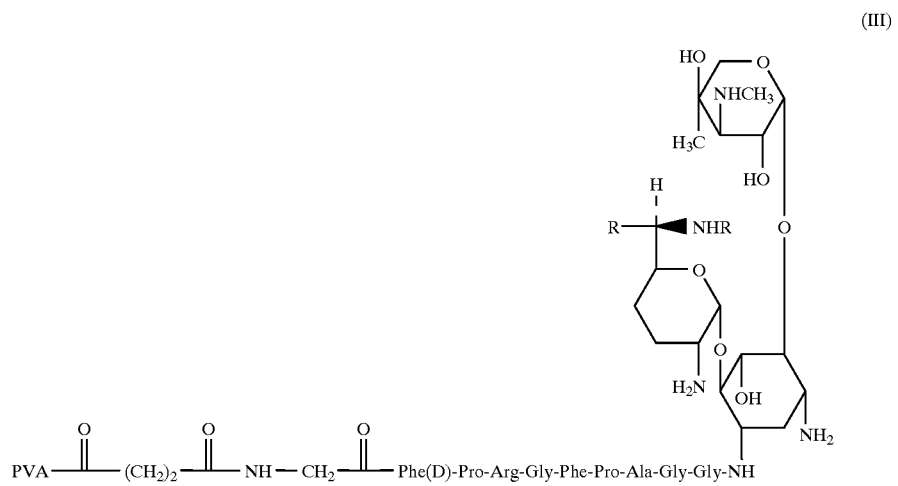

wherein PVA represents polyvinyl alcohol gel.

(1) In 300 g of dimethylsulfoxide, 10 g of the partially saponified polyvinyl alcohol obtained above in (2) of Referential Example 1 were dissolved, followed by the addition of 1.64 g of succinic anhydride and 0.64 g of pyridine. The resulting mixture was reacted at 70° C. for 4 hours. About 330 g of the resulting solution were cast into a 25 cm×25 cm-polystyrene tray, followed by immersion into water gently, whereby an intermediate having a portion of the first spacer (Sp1) (which had not yet finished binding) bound with a water-swelling polymer gel (A) was obtained.

(2) Separately from the above (1), a Gly-Phe(D)-Pro-Arg (Mtr)-Gly-Phe-Pro-Ala-Gly-Gly-HMP resin was obtained by Fmoc chemistry by using a full automatic peptide synthesizer ("Model 431A", trade name; product of Applied Biosystems Japan). The resulting resin was treated for 6 hours with 10 ml of trifluoroacetic acid containing 5% of water, 5% of thioanisole, 7.5% of phenol and 2.5% of ethanedithiol. Diethyl ether was added to the resulting solution to cause precipitation, followed by washing with diethyl ether several times, whereby Gly-Phe(D)-Pro-Arg-Gly-Phe-Pro-Ala-Gly-Gly- in which the remaining portion of the first spacer (Sp1), cleavable group (E) and second spacer (Sp2) had been bound was obtained.

In the above formula, Arg(Mtr) represents $N^g$-4-methoxy-2,3,6,-trimethylbenzenesulfonyl-L-arginine residue and HMP resin represents a powdery resin (HMP resin; product of Applied Biosystems Japan) composed of a styrene-divinylbenzene copolymer (a component ratio of styrene to divinylbenzene: 99 to 1) containing a 4-hydroxymethylphenoxy-methyl group in an amount of 0.89 mmol/g (resin).

(3) The intermediate (10 g) obtained in (1) by binding a water-swelling polymer gel with a portion of the first spacer (Sp1) was washed with dimethylformamide to substitute the water content in the gel by dimethylformamide. To the substituted intermediate, 0.45 g of N-hydroxysuccinimide and 1.8 g of 1-ethyl-3-(3-dimethylaminopropyl)-carbodiimide hydrochloride (EDC.HCl) were added, followed by agitation overnight. The reaction mixture was washed with water several time, followed by the addition of 50 mg of Gly-Phe(D)-Pro-Arg-Gly-Phe-Pro-Ala-Gly-Gly- obtained above in (2) and 9 μl of diisopropylethylamine. The resulting mixture was agitated overnight, whereby an intermediate [that is, a polymer gel (Ia) to be bound with a drug] in which the first spacer (Sp1), the cleavable group (E) and the second spacer (Sp2) had been bound with a water-swelling polymer gel (A) in order of mention was obtained. It was possible to provide the resulting intermediate as was to storage or distribution.

(4) The intermediate [polymer gel (Ia)] obtained above in (3) was washed with water several times, and then with a 0.05M aqueous solution of sodium bicarbonate once, followed by the addition of 0.6 g of gentamycin and 0.2 g of EDC.HC. The resulting mixture was agitated overnight. The reaction mixture was then washed sufficiently with water, whereby a polymer gel which was represented by the above formula (III) and in which the first spacer (Sp1), the cleavable group (E), the second spacer (Sp2) and a drug (gentamycin) had been bound with a water-swelling polymer gel (A) in order of mention was obtained.

EXAMPLE 2

Preparation of a Polymer Gel

In Example 2, prepared was a polymer gel comprising a gel composed of the polyvinyl alcohol obtained above in Referential Example 1(2) as a water-swelling polymer gel (A), —CO—(CH$_2$)$_2$—CO—NH—CH$_2$—CO— as the first spacer (Sp1), -Val-Pro-Arg-Gly-Val-Pro-Arg-Gly-Val-Pro-Arg- as a cleavable group (E), -Gly-Gly- as the second spacer (Sp2) and gentamycin as a drug; and being represented by the following formula (IV):

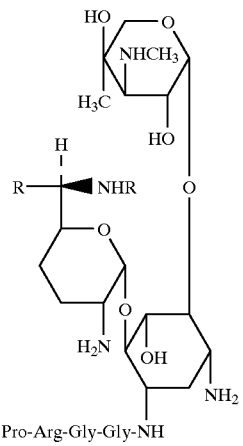

wherein PVA represents polyvinyl alcohol gel.

(1) Described specifically, an intermediate having the water-swelling polymer gel (A) bound with a portion of the first spacer (Sp1) (which had not yet finished binding) was prepared in a similar manner to Example 1(1). (2) Separately from (1), in a similar manner to Example 1(2), a Gly-Val-Pro-Arg(Mtr)-Gly-Val-Pro-Arg(Mtr)-Gly-Val-Pro-Arg (Mtr)-Gly-Gly-HMP resin was prepared instead of the Gly-Phe(D)-Pro-Arg(Mtr)-Gly-Phe-Pro-Ala-Gly-Gly-HMP resin obtained in Example 1(2) by Fmoc chemistry by using a full automatic peptide synthesizer "Model 431A". The resulting resin was treated as in Example 1(2), whereby Gly-Val-Pro-Arg-Gly-Val-Pro-Arg-Gly-Val-Pro-Arg-Gly-Gly- in which the remaining portion of the first spacer (Sp1), the cleavable group (E) and the second spacer (Sp2) had been bound together was obtained.

(3) In a similar manner to Example 1(3), the intermediate obtained above in (1) was bound with the Gly-Val-Pro-Arg-Gly-Val-Pro-Arg-Gly-Val-Pro-Arg-Gly-Gly- obtained above in (2), whereby an intermediate [a polymer gel (Ia) to be bound with a drug] in which the first spacer (Sp1), the cleavable group (E) and the second spacer (Sp2) had been bound in order of mention with the water-swelling polymer gel (A) was prepared. Gentamycin was bound with the resulting intermediate in a similar manner to Example 1(4), whereby the polymer gel represented by the above formula (IV) was obtained.

EXAMPLE 3

Preparation of a Polymer Gel

In Example 3, prepared was a polymer gel comprising a gel composed of the polyvinyl alcohol obtained above in Referential Example 1(2) as a water-swelling polymer gel (A), —CO—(CH$_2$)$_2$—CO—NH—CH$_2$—CO— as the first spacer (Sp1), -Phe-Pro-Arg-Gly-Phe-Pro-Arg- as a cleavable group (E), -Gly-Gly- as the second spacer (Sp2) and gentamycin as a drug; and being represented by the following formula (V):

(V)

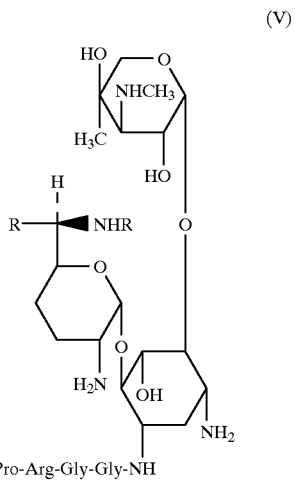

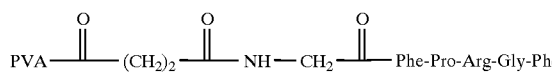
PVA—CO—(CH$_2$)$_2$—CO—NH—CH$_2$—CO—Phe-Pro-Arg-Gly-Phe-Pro-Arg-Gly-Gly-NH wherein PVA represents polyvinyl alcohol gel.

(1) Described specifically, an intermediate having the water-swelling polymer gel (A) bound with a portion of the first spacer (Sp1) (which had not yet finished binding) was prepared in a similar manner to Example 1(1).

(2) Separately from (1), in a similar manner to Example 1(2), a Gly-Phe-Pro-Arg(Mtr)-Gly-Phe-Pro-Arg-Gly-Gly-HMP resin was prepared by Fmoc chemistry by using a full automatic peptide synthesizer "Model 431A". The resulting resin was treated as in Example 1(2), whereby Gly-Val-Pro-Arg-Gly-Val-Pro-Arg-Gly-Val-Pro-Arg-Gly-Gly- in which the remaining portion of the first spacer (Sp1), the cleavable group (E) and the second spacer (Sp2) had been bound together was obtained.

(3) In a similar manner to Example 1(3), the intermediate obtained above in (1) was bound with the Gly-Phe-Pro-Arg-Gly-Phe-Pro-Arg-Gly-Gly- obtained above in (2), whereby an intermediate [a polymer gel (Ia) to be bound with a drug] in which the first spacer (Sp1), the cleavable group (E) and the second spacer (Sp2) had been bound in order of mention with the water-swelling polymer gel (A) was prepared. Gentamycin was bound with the resulting intermediate in a similar manner to Example 1(4), whereby the polymer gel represented by the above formula (V) was obtained.

EXAMPLE 4

Preparation of Polymer Gel

In Example 4, prepared was a polymer gel comprising a gel composed of the polyvinyl alcohol obtained above in Referential Example 1(2) as a water-swelling polymer gel (A), —CO—(CH$_2$)$_2$—CO—NH—CH$_2$—CO— as the first spacer (Sp1), -Phe(D)-Pro-Arg- as a cleavable group (E), -Gly-Phe-Pro-Ala- as the second spacer (Sp2) and norfloxacin as a drug; and being represented by the following formula (VI):

(VI)

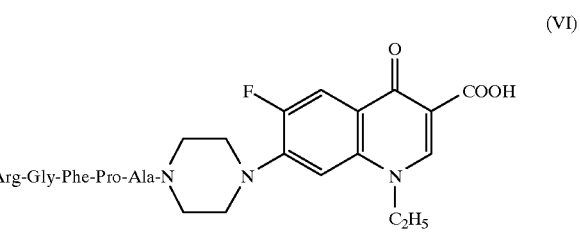

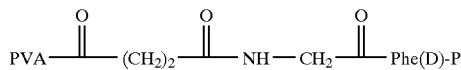
PVA—CO—(CH$_2$)$_2$—CO—NH—CH$_2$—CO—Phe(D)-Pro-Arg-Gly-Phe-Pro-Ala-N wherein PVA represents polyvinyl alcohol gel.

(1) Described specifically, an intermediate having the water-swelling polymer gel (A) bound with a portion of the first spacer (Sp1) (which had not yet finished binding) was prepared in a similar manner to Example 1(1).

(2) Separately from (1), in a similar manner to Example 1(2), a Gly-Phe(D)-Pro-Arg(Mtr)-Gly-Phe-Pro-Ala-HMP resin was prepared by Fmoc chemistry by using a full automatic peptide synthesizer "Model 431A". The resulting resin was treated as in Example 1(2), whereby Gly-Phe(D)-

Pro-Arg-Gly-Phe-Pro-Ala- in which the remaining portion of the first spacer (Sp1), the cleavable group (E) and the second spacer (Sp2) had been bound together was obtained.

(3) In a similar manner to Example 1(3), 10 g of the intermediate obtained above in (1) were bound with 50 mg of the Gly-Phe(D)-Pro-Arg-Gly-Phe-Pro-Ala- obtained above in (2), whereby an intermediate [a polymer gel (Ia) to be bound with a drug] in which the first spacer (Sp1), the cleavable group (E) and the second spacer (Sp2) had been bound in order of mention with the water-swelling polymer gel (A) was prepared.

(4) The intermediate [polymer gel (Ia)] obtained above in (3) was washed with water several times, and then with dimethylformamide several times to substitute the water content in the gel with dimethylformamide, followed by the addition of 0.46 g of N-hydroxysuccinimide and 1.8 g of 1-ethyl-3-(3-dimethylaminopropyl)-carbodiimide hydrochloride (EDC.HC). The resulting mixture was agitated overnight. The reaction mixture was then washed with dimethylformamide several times, followed by the addition of a solution of 100 mg of norfloxacin and 20 µl of diisopropylethylamine in 20 ml of dimethylformamide. The resulting mixture was agitated overnight. The reaction mixture was washed sufficiently with water, whereby a polymer gel which was represented by the above formula (VI) and in which the first spacer (Sp1), the cleavable group (E), the second spacer (Sp2) and the drug (norfloxacin) had been bound with the water-swelling polymer gel (A) in order of mention was obtained.

EXAMPLE 5
Preparation of Polymer Gel

In Example 5, prepared was a polymer gel comprising a gel composed of the polyvinyl alcohol obtained above in Referential Example 1(2) as a water-swelling polymer gel (A). —CO—(CH$_2$)$_2$—CO— as the first spacer (Sp1), -Gly-Pro-Leu-Gly-Pro- as a cleavable group (E), -Gly-Gly- as the second spacer (Sp2) and TGFP as a drug; and being represented by the following formula (VII):

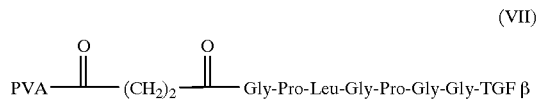

(VII)

wherein PVA represents polyvinyl alcohol gel.

(1) Described specifically, an intermediate having the water-swelling polymer gel (A) bound with a portion of the first spacer (Sp1) (which had not yet finished binding) was prepared in a similar manner to Example 1(1).

(2) Separately from (1), in a similar manner to Example 1(2), a Gly-Pro-Leu-Gly-Pro-Gly-Gly-HMP resin was prepared by Fmoc chemistry by using a full automatic peptide synthesizer "Model 431A". The resulting resin was treated as in Example 1(2), whereby Gly-Pro-Leu-Gly-Pro-Gly-Gly- in which the remaining portion of the first spacer (Sp1), the cleavable group (E) and the second spacer (Sp2) had been bound together was obtained.

(3) In a similar manner to Example 1(3), 1 g of the intermediate obtained above in (1) was bound with 5 mg of the Gly-Pro-Leu-Gly-Pro-Gly-Gly- obtained above in (2), whereby an intermediate [a polymer gel (Ia) to be bound with a drug] in which the first spacer (Sp1), the cleavable group (E) and the second spacer (Sp2) had been bound in order of mention with the water-swelling polymer gel (A) was prepared.

(4) The intermediate [polymer gel (Ia)] obtained above in (3) was washed with water several times, and then with dimethylformamide several times to substitute the water content in the gel with dimethylformamide, followed by the addition of 46 mg of N-hydroxysuccinimide and 0.18 g of 1-ethyl-3-(3-dimethylaminopropyl)-carbodiimide hydrochloride (EDC.HC). The resulting mixture was agitated overnight. The reaction mixture was then washed with water several times, followed by the addition of a solution of 1 µg of TGFβ in 1 ml of water. The resulting mixture was agitated overnight. The reaction mixture was washed sufficiently with water, whereby a polymer gel which was represented by the above formula (VII) and in which the first spacer (Sp1), the cleavable group (E), the second spacer (Sp2) and the drug (TGFP) had been bound with the water-swelling polymer gel (A) in order of mention was obtained.

Comparative Example 1
Preparation of Polymer Gel

In Comparative Example 1, prepared was a polymer gel in which —CO—(CH$_2$)—CO— as a spacer and gentamycin as a drug had been bound in order of mention with a gel composed of the polyvinyl alcohol obtained above in Referential Example 1(2) as a water-swelling polymer gel (A) and which is represented by the following formula (VIII):

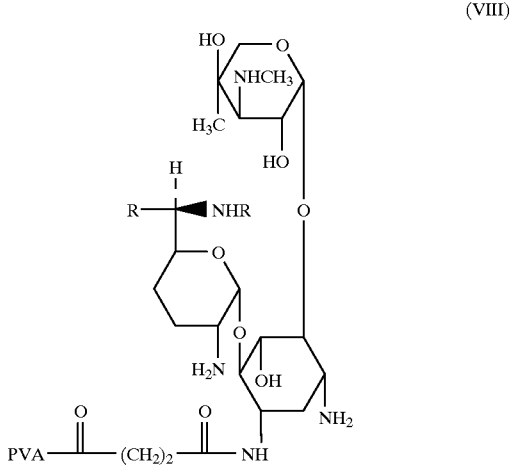

(VIII)

wherein PVA represents polyvinyl alcohol gel.

Described specifically, an intermediate having the water-swelling polymer gel (A) bound with the spacer was prepared in a similar manner to Example 1(1). The resulting intermediate (10 g) was washed with water several times and then with a 0.05M aqueous solution of sodium bicarbonate once, followed by the addition of 2.4 g of gentamycin and 0.8 g of EDC.HC. The resulting mixture was agitated overnight. The reaction mixture was washed sufficiently with water, whereby a polymer gel of the above formula (VIII) in which the spacer and the drug (gentamycin) had been bound in order of mention with the water-swelling polymer gel (A) was obtained.

Referential Example 2
Preparation of Polymer Gel

In Referential Example 2, prepared was a polymer gel in which —CO—(CH$_2$)—CO—NH—CH$_2$—CO— as a spacer, -Val-Pro-Arg- as a cleavable group (E) and gentamycin as a drug had been bound in order of mention with a gel composed of the polyvinyl alcohol obtained above in Referential Example 1(2) as a water-swelling polymer gel (A), and which is represented by the following formula (IX):

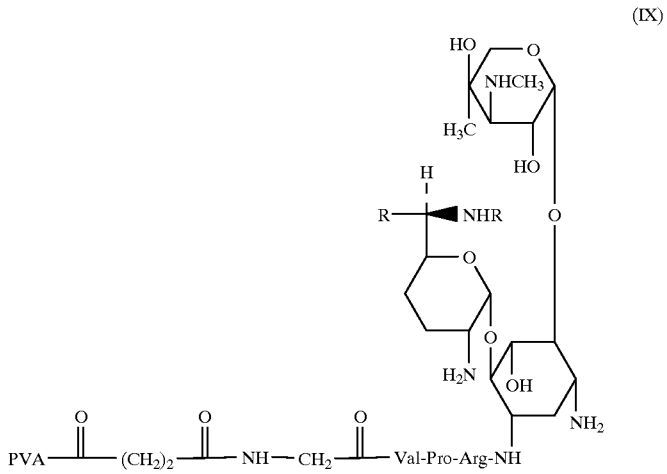

(IX)

wherein polyvinyl alcohol represents polyvinyl alcohol gel.

(1) Described specifically, an intermediate having the water-swelling polymer gel (A) bound with a portion of the spacer (which had not yet finished binding was prepared in a similar manner to Example 1(1).

(2) Separately from (1), in a similar manner to Example 1(2), Gly-Val-Pro-Arg(Mtr)-HMP resin was prepared by Fmoc chemistry by using a full automatic peptide synthesizer "Model 431A". The resulting resin was treated as in Example 1(2), whereby Gly-Val-Pro-Arg- in which the remaining portion of the spacer and the cleavable group (E) had been bound together was obtained.

(3) In a similar manner to Example 1(3), 10 g of the intermediate obtained above in (1) were bound with 50 mg of the Gly-Val-Pro-Arg- obtained above in (2), whereby an intermediate in which the spacer and the cleavable group (E) had been bound in order of mention with the water-swelling polymer gel (A) was prepared.

(4) With the intermediate obtained above in (3), gentamycin was bound in a similar manner to Example 1(4), whereby a polymer gel of the formula (IX) in which the spacer, the cleavable group (E) and the drug (gentamycin) had been bound with the water-swelling polymer gel (A) in order of mention was obtained.

Test 1
Drug Release Test by Using Pseudo Exudate From Infected Wound (1) The polymer gels obtained in Examples 1 to 4, Comparative Example 1 and Referential Example 2 were weighed, each in an amount of 0.1 g. To each of the gels, 150 $\mu$l of PBS (a 0.01 M phosphate buffer containing 0.15M NaCl; pH 7.4), 50 $\mu$l of the supernatant of Staphylococcus aureus cultured and 50 $\mu$l of the human plasma were added, followed by agitation at 37° C. overnight. The supernatant (75 $\mu$l) of the resulting reaction mixture was immersed in a filter paper having a diameter of 8 mm. The filter paper was placed on a Brain-Heart-Infusion agar medium plate (diameter: 10 cm) to which $2 \times 10^6$ cfu of Staphylococcus aureus had been inoculated, followed by culturing overnight at 37° C. The diameter of the zone of growth inhibition formed on the periphery of the filter paper was measured.

(2) A filter paper of the same diameter was, on the other hand, immersed with 75 $\mu$l of an aqueous solution of gentamycin (10 $\mu$g/ml) and placed on a Brain-Heart-Infusion agar medium plate (diameter: 10 cm) to which $2 \times 10^6$ cfu of Staphylococcus aureus had been inoculated, followed by culturing overnight at 37° C. The diameter of the zone of growth inhibition formed on the periphery of the filter paper was measured.

(3) A release amount of the antibacterial agent per hour was determined by calculating the amount of the antibacterial agent released to the supernatant in (1) based on the ratio of the diameter of the zone of the growth inhibition obtained above in (2) to that obtained above in (1). The results are shown in Table 2.

TABLE 2

| | Amount of an antibacterial agent released ($\mu$g/g gel · 1 hour) |
| --- | --- |
| Example 1 | 1.0 |
| Example 2 | 0.5 |
| Example 3 | 0.6 |
| Example 4 | 0.8 |
| Comparative Example 1 | 0 |
| Referential Example 2 | 0.2 |

Test 2
Healing Test of Wounds with Bacterial Infection by Using Rats (1) Together with a 10 mg/ml aqueous solution of montmorillonite, Staphylococcus aureus ($10^9$ cfu) was inoculated on an about 2-cm diameter pocket wound made on the back of a rat. Forty eight hours later, the pocket wound was washed with physiological saline, followed by insertion of the polymer gel obtained in Example 1 or Comparative Example 1 in an amount of 1 g. Twenty four hours later, a predetermined amount of the tissue was sampled from the wound, followed by homogenization in PBS. The resulting PBS solution diluted to a predetermined ratio was uniformly applied on a Brain-Heart-Infusion agar medium plate (diameter: 10 cm) and cultured at 37° C. overnight. Based on the number of the colonies so formed, the number of the bacteria in the tissue was measured. The number of the bacteria in the pocket wound inserted by the polymer gel obtained in Example 1 was $6.7 \times 10^4 \pm 8.9 \times 10^4$ cfu/g.tissue, while that inserted by the polymer gel obtained in Comparative Example 1 was $1.2 \times 10^7 \pm 1.1 \times 10^6$ cfu/g.tissue.

(2) The number of bacteria in the wound treated in a similar manner to the above (1) except that the polymer gel was not inserted in the pocket wound was $1.1 \times 10^8 \pm 2.0 \times 10^7$ cfu/g.tissue.

(3) It can be understood from the above results that compared with the case where no polymer gel was used, the number of bacteria decreased to about 1/1000 when the polymer gel of Example 1 was used, while that decreased to only about 1/10 when the polymer gel of Comparative Example 1 was used.

Test 3

Release Test of TGFβ by a Model Enzyme (Collagenase) of Inflammatory Exudate

To 0.1 g of the polymer gel obtained in Example 5, 1 ml of a solution of 0.1 U/ml of collagenase in PBS was added, followed by agitation at 37° C. for 2 hours. The TGFβ concentration in the supernatant was measured using an EIA kit for the measurement of TGFβ ["PREDICTA™ Human TGF-β1 ELISA KIT"; product of Genzyme Diagnostics]. As a result, an amount of TGFβ released per hour calculated from the TGFβ concentration was about 7 ng/g gel.

What is claimed is:

1. A polymer gel for medical use produced by binding a drug with a water-swelling polymer gel in a sequence represented by the following formula (I):

A-Sp1-E-Sp2-G      (I)

wherein A represents a water-swelling polymer gel, Sp1 represents a first peptide-containing spacer, E represents a cleavable group with the main chain to be cleaved via an enzymatic reaction, Sp2 represents a second peptide-containing spacer and G represents a drug.

2. A polymer gel for medical use which is represented by the following formula (Ia):

A-Sp1-E-Sp2'      (I)

wherein A represents a water-swelling polymer gel, Sp1 represents a first peptide-containing spacer, E represents a cleavable group with the main chain to be cleaved via an enzymatic reaction, Sp2' represents a second peptide-containing spacer precursor and permits the binding of a drug with the water-swelling polymer gel through the first spacer (Sp1), a cleavable group (E) and the second spacer (Sp2) with the proviso that Sp2 represents the second spacer formed when the second spacer precursor (Sp2') and the drug are bound.

3. A polymer gel for medical use according to claim 1 or 2, wherein any one of the first spacer (Sp1), second spacer (Sp2) and second spacer precursor (Sp2') is a molecular chain with the total number of carbon atoms, nitrogen atoms and oxygen atoms contained in the main chain being at least 4.

4. A polymer gel for medical use according to claim 1, wherein the cleavable group (E) with the main chain to be cleaved via an enzymatic reaction is derived from 2- to 8-mer oligopeptides.

5. A polymer gel for medical use according to claim 1, wherein the water-swelling polymer gel comprises a polyvinyl alcohol.

6. The polymer gel for medical use according to claim 2, wherein the cleavable group (E) is derived from 2- to 8-mer oligopeptides.

7. The polymer gel for medical use according to claim 2, wherein the water-swelling polymer gel comprises a polyvinyl alcohol.

8. The polymer gel for medical use according to claim 1, wherein A is a polyvinyl alcohol gel, Sp1 is —CO—(CH$_2$)$_2$—CO—NH—CH$_2$—CO—, E is -Phe(D)-Pro-Arg-, Sp2 is -Gly-Phe-Pro-Ala-Gly-Gly-, and the drug G is gentamycin.

9. The polymer gel for medical use according to claim 2, wherein A is a polyvinyl alcohol gel, Sp1 is —CO—(CH$_2$)$_2$—CO—NH—CH$_2$—CO—, E is -Phe(D)-Pro-Arg-, Sp2 is -Gly-Phe-Pro-Ala-Gly-Gly-, and the drug is gentamycin.

* * * * *